United States Patent [19]

Takematsu et al.

[11] Patent Number: 4,767,442
[45] Date of Patent: Aug. 30, 1988

[54] INCREASING THE YIELD OF CEREALS BY MEANS OF BRASSINOLIDE DERIVATIVES

[75] Inventors: Tetsuo Takematsu, Utsunomiya; Nobuo Ikekawa, Musashino; Atsuhiko Shida, Koga, all of Japan

[73] Assignee: Nippon Kayaku Kabushiki Kaisha, Tokyo, Japan

[21] Appl. No.: 906,378

[22] Filed: Sep. 12, 1986

[30] Foreign Application Priority Data

Sep. 19, 1985 [JP] Japan .................... 60-208140

[51] Int. Cl.⁴ .......................................... A01N 43/04
[52] U.S. Cl. ............................................. 71/88
[58] Field of Search ................................ 71/88

[56] References Cited

U.S. PATENT DOCUMENTS 4,346,226  8/1982  Thompson et al. ............ 411/258

FOREIGN PATENT DOCUMENTS 1173659  9/1984  Canada .
58-90578  5/1983  Japan .

OTHER PUBLICATIONS

Kagaku, vol. 39, No. 2 (1984), pp. 129–131.
Gregory, Chem. Abst., vol. 95 (1981), 36959v.
Meudt et al, Chem. Abst., vol. 102 (1985), 19625d.
Gregory, American Journal of Botany, 68(4): 586–588 (1981).
Japanese Journal of Crop Sciences, vol. 53 Extra Issue 2, 165–169 (1984).

Primary Examiner—Catherine L. Mills
Attorney, Agent, or Firm—Henry C. Nields

[57] ABSTRACT

The yield of a cereal is increased by application of an agent selected from brassinolide derivatives of the formulae:

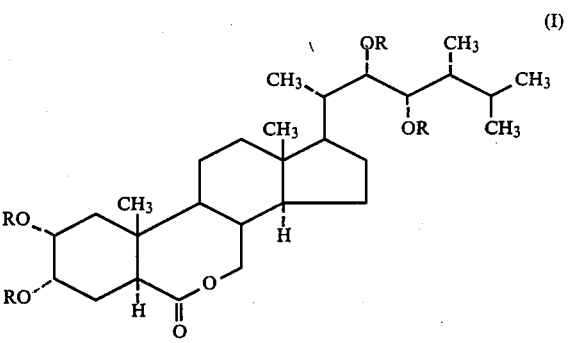

and

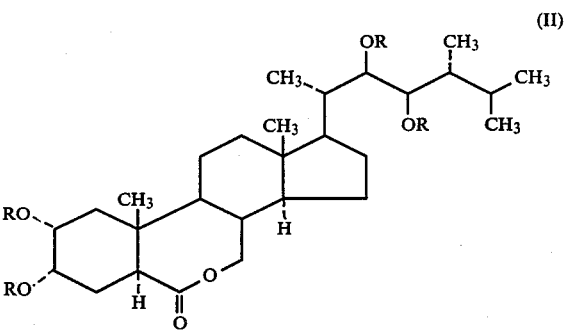

wherein R is hydrogen or acetyl.

2 Claims, No Drawings

INCREASING THE YIELD OF CEREALS BY MEANS OF BRASSINOLIDE DERIVATIVES

DETAILED DESCRIPTION OF THE INVENTION

The present invention relates to the use of brassinolide derivatives (brassinosteroids) which have the effect of promoting plant growth, or in more detail, to a composition comprising said derivatives as active ingredients for increasing the yield of cereals and to a method of increasing the yield thereof using said derivatives.

The fact that brassinolide derivatives have the effect of promoting plant growth is known, for example, from publications such as KAGAKU Vol. 39, No. 2, pp. 129–131 (1984), and Japanese Patent Kokai No. 58-90578. It is also known that seedless grapes are harvested and fruit bearing is promoted by spreading plant hormones such as auxins, gibberellin or cytokinins at the time of flowering of the fruit.

Recently, owing to growth of world population, there has been vigorous research for the purpose of increasing the yield of crops, especially staple crops such as rice, wheat and maize. Among those investigations, there have been experiments to improve the crop-yield-increase effect which results from the use of brassinolide derivatives (recently observed) and plant hormones, but there have not yet been any reports of remarkable effectiveness with respect to cereals.

The object of this invention is to increase efficiently the yield especially of cereals among staple crops.

The inventors of the present invention have intensively investigated the relationship between the increase of the yield of the cereal and the physiologically active effect of the brassiniolide derivatives which are said to have a plant-growth action.

In consequence of this research, the inventors have found that if at least one selected from the group consisting of brassinolide derivatives of the formulae:

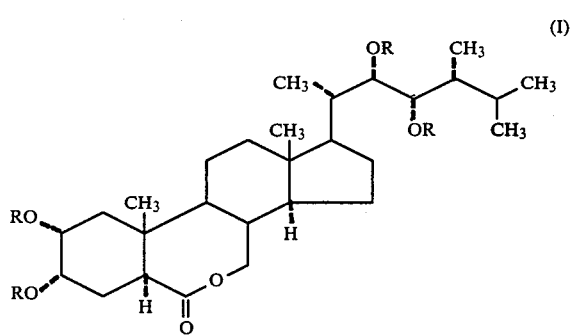

and

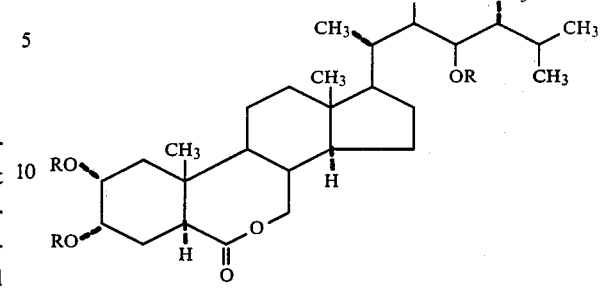

wherein R represents a hydrogen atom or acetyl group. is applied to cereals at the seed stage, at from immediately after germination of seeds to the five-foliage level, or at about the time of flowering, there is revealed a remarkable increase in the yield of said cereals. Thus the inventors have completed the present invention.

The brassinolide derivatives of the present invention represented by the formulae (I) and (II) can be prepared for example by the process described in Japanese Patent Kokai No. 60-139685, and as examples of such compound there can be mentioned as follows:

(22R,23R,24R)-2α,3α,22,23-Tetrahydroxy-B-homo-7-oxa-5α-ergostan-6-one (III).

melting point: 256°~257° C. (256°~257° C. by literature).

EI-MS m/z: 465(M+-15), 462(M+-18), 447, 409, 380 (M+-101, $C_{22}$ - $C_{23}$ fission +H, base peak), 379, 361, 350, 343, 331, 325, 322, 313, 307, 303, 285, 177, 173, 155, 131, 101, 71, 43.

Emitter CI-MS(isobutane) m/z: 481(M+ +1, base peak), 463, 445.

$^1$H-NMR(CDCl$_3$)δ: 0.69 (3H, s, 18-H$_3$), 1.98 (3H, s, acetyl), 2.02 (6H, s, 2 acetyls), 2.09 (3H, s, acetyl), 3.00 (1H, dd, J=13 and 6 Hz, 5α-H) 4.07 (2H, m, 7-H$_2$), 4.70~5.50 (4H, m, 2-H, 3-H, 22-H and 23-H) (sample tested as tetraacetate).

Elementary analysis:

|  | C (%) | H (%) |
| --- | --- | --- |
| found: | 70.01 | 9.92 |
| calculated: (as $C_{28}H_{48}O_6$) | 70.03 | 9.85 | and the acetyl derivatives thereof, for example, tetraacetate.

(22S,23S,24R)-2α, 3α,22,23-Tetrahydroxy-B-homo-7-oxa-5α-ergostan-6-one (IV).

melting point: 193°~195° C. (193°~195° C. by literature).

EI-MS m/z: 465(M+-15), 465(M+-18), 447, 409, 380, 379, 361, 350, 343, 331, 325, 322, 313, 307, 285, 177, 173, 155, 131, 101, 71, 43.

Emitter-CI-MS (isobutane) m/z: 481(M+ +1, base peak), 463, 445.

$^1$H-NMR(CDCl$_3$)δ: 0.67 (3H, s, 18-H$_3$), 1.93 (3H, s, acetyl), 2.03 (9H, s, 3 acetyls), 3.00 (1H, dd, J=13 and 6 Hz, 5α-H) 4.07 (2H, m, 7-H$_2$) 4.50~5.50 (4H, m, 2-H, 3-H, 22-H and 23-H) (sample tested as tetraacetate).

Elementary analysis:

|  | C (%) | H (%) |
|---|---|---|
| found: | 69.88 | 9.87 |
| calculated: (as $C_{28}H_{48}O_6$) | 70.03 | 9.85 | and the acetyl derivatives thereof, for example, tetraacetate.

In accordance with the invention, the brassinolide derivatives of the formulae (I) and (II) can be used either alone or in the admixture of two or more of said derivatives by dilution with water in low concentration. Alternatively, they may be mixed with adjuvants to make formulations such as dust, granule, grain, wettable powder, flowable suspension and emulsion concentrate by means of usual procedures in the agro-chemical manufacture, to promote or stabilize the effect of said derivatives.

Those adjuvants mentioned above include carriers, (diluents) and other adjuvants such as spreaders, emulsifiers, wetting agents, dispersing agents, fixing agents and disintegrators.

As liquid carriers there can be mentioned aromatic hydrocarbons such as toluene and xylene, alcohols such as methanol, butanol and glycol, ketones such as acetone, amides such as dimethylformamide, sulfoxides such as dimethylsulfoxide, methylnaphthalene, cyclohexane, animal and vegetable oils, fatty acids and their esters, etc.

As solid carriers there are mentioned clay, kaolin, talc, diatomaceous earth, silica, calcium carbonate, montmorillonite, bentonite, feldspar, quartz, alumina, sawdust, etc.

As emulsifiers or dispersing agents surfactants are generally used. They include anionic, cationic, nonionic and amphoteric surfactants such as sodium higher alkylsulfates, stearyltrimethylammonium chloride, polyoxyethylenealkylphenyl ether, lauryl betaine, etc.

In the case of use of those carriers, it is important to scrutinize carefully and employ those which are the most suitable for promoting the efficacy of the brassinolide derivatives.

Any of said formulations can be not only alone, but also may be mixed with fungicides, insecticides, plant growth regulators, acaricides, horticultural pesticides, soil disinfectants, soil improvement agents or nematocides, and further can be used in combination with fertilizers or other herbicides.

The content of a brassinolide derivative as active ingredient in the composition for increasing the yield of cereals of the invention, varies with types of formulation, methods of applications and other conditions, and generally it is 0.01 to 95 weight %, preferably 0.01 to 50 weight %, though sometimes the active compound may be used alone.

In the present invention the term "cereal" may have the same meaning such as "graminaceous plant", "grain crop" and etc. and "cereal" can include rice, maize (corn), wheat, barley, oat and etc.

In the present invention the term "apply" can include "spread", "spray", "sprinkle" or "soak".

It has been remarkably demonstrated that the brassinolide derivatives employed in the present invention have the effect of increasing crop yield even in very small amounts, and the amount applied is generally 0.00001 to 100 mg/are preferably 0.01 to 10 mg/are. When they are applied as a solution or dispersion in water or an organic solvent, 0.0001 to 10 ppm is preferable. Moreover, when applying it is especially preferred to spread on those stem and leaves including flowers or ears.

When applying the composition of the invention for increasing the yield of cereals, it is important to carry out the applying treatment at about the time of flowering of said crops. As used herein, the phrase "at about the time of flowering" means the period from the beginning of formation of reproductive cells to the ripening of seeds by completion of fertilization. Taking rice as an example, said period is from the filling of the ears to the harvest after finishing fertilization of the last grain flower in the ear.

From the time of reproductive cell formation to the perfection of seeds upon fertilization, the translocation and removal of nutrients or energy within the body of the plant to reproductive cells or seeds are extremely active, and in order also to control this, various substances such as plant hormones participate intimately. If such translocation and removal can moreover be activated and increase the ripe seeds, it can be considered possible to ultimately increase the crop yield.

Furthermore, the period from formation of the ootid and spermatid to fertilization is an especially suitable time to exercise influence directly over the reproductive cells. Within that period, the time of flowering and fertilization is a time when reproductive cells are exposed directly to the surroundings, so that they may be regarded as very susceptible to the influence of even extremely small amounts of active compounds.

Consequently, the inventors suggested that with respect to crops whose seeds are harvested, such as cereals, this time may be seen as being allied with maximum increase in yield, and when the brassinolide derivatives of the formulae (I) and (II) are spread, a very high efficacy of increased yield of crops was found. Probably the brassinolide derivatives according to the invention may be thought of as accomplishing the effect of promoting the cell expansion action of plant hormones such as indole-acetic acid, gibberellin, cytokinins, etc.

Another characteristic of this invention is the achievement of great efficacy of yield increase by means of a single applying (spreading) of even extremely small amounts by matching the applying (spreading) time to the time of flowering.

When increasing the yield of cereals it is important to cause good growth at the time of five-foliage level immediately after germination of seeds, at which time the growth of crops is very sensitive and susceptible to the surrounding conditions.

It was found that brassinolide derivatives made the crops grow favorably by seed-soaking, root treatment, stem treatment, etc. with a slight amount during such period.

According to the present invention, the effective increase in yield of crops such as rice, wheat and maize of 2 to 37% can be achieved.

Detailed explanation will be illustrated in Formulation Examples of the present invention below. Wherein the kind and mixing proportion of adjuvants are not limited thereby, but may be used under wide range. The word "part" in examples means part by weight.

FORMULATION EXAMPLE 1

Emulsion 35 parts of a mixture (1:1) of xylene and methylnaphthalene are added to a mixture of 25 parts of Compound [III] and 25 parts of Compound [IV] to form a solution and the solution is further mixed with 15 parts of a mixture (8:2) of polyoxyethylenealkylphenyl ether and calcium alkylbenzenesulfonate to obtain an emulsion.

FORMULATION EXAMPLE 2

Dust 5 parts of Compound [IV] are mixed with 95 parts of clay and pulverized to obtain a dust.

FORMULATION EXAMPLE 3

Wettable powder 1 part of Compound [IV] are mixed with 10 parts of diatomaceous earth and 71 parts of kaolin as the carriers and further uniformly blended with 18 parts of a mixture of sodium laurylsulfate and sodium 2,2-dinaphthylmethanesulfonate, and thereafter finely pulverized to obtain a wettable powder.

FORMULATION EXAMPLE 4

Granule 0.01 part of a fine dust of Compound [III] is spread and coated on 98.4 parts of grains (16 to 32 mesh) of silica to obtain a granule, by using a methanol solution of 1.5 parts of polyvinylacetate as the binding agent in a proper mixer.

TEST EXAMPLE 1

A Wagner pot of 1/5000 are were filled with field soil, and after being manured, 10 seeds of wheat were sown therein. At the 2- to 3-leaf stage the plants were thinned out and 5 individuals per pot, and at the flowering stage, they were treated by spraying at 5 m/pot a solution with concentration listed in Table 1 which was obtained from a wettable powder containing 1% of the brassinolide derivative.

As is shown in Table 1, the increase of panicle weight was found to be 2 to 33% at concentrations of 0.001 to 1 ppm, which was very much higher than the untreated wheat.

TABLE 1

Effect on the ear weight of wheat

| Test Compound | Concentration (ppm) | Panicle weight (ratio to the untreated plot) g/panicle | Seed weight (ratio to the untreated plot) g/panicle |
|---|---|---|---|
| III | 0.001 | 1.37 (126) | 1.07 (130) |
|  | 0.01 | 1.43 (132) | 1.04 (127) |
|  | 0.1 | 1.39 (128) | 1.12 (137) |
|  | 1 | 1.35 (125) | 1.03 (126) |
| IV | 0.001 | 1.11 (102) | 0.85 (104) |
|  | 0.01 | 1.26 (116) | 1.00 (122) |
|  | 0.1 | 1.44 (133) | 1.12 (137) |
|  | 1 | 1.31 (121) | 1.01 (123) |
| Untreated |  | 1.08 (100) | 0.82 (100) |

TEST EXAMPLE 2

Effect on Seed of Maize

Maize (Honey Bantam) was sown on June 7, and at time of silk extract of its female ear, was treated by spraying 1000 l/ha with 0.01, 0.1 and 1 ppm of compounds of formulae (III) and (IV) respectively, to each of which was added an spreader (1000 times by weight).

On the 43rd day after the treatment, it was harvested, and the total length of grain ear (female ear) and the longest part of the sterile ear were measured. As is shown by the result set out in the Table 2, the sterile parts diminished to about one-half compared to the untreated maize, so that fructification became more favorable.

TABLE 2

Effect on maize of Brassinolide derivatives

| Compound | Concentration ppm | Total length cm | Sterile part cm | Ratio of the sterile part to total length % |
|---|---|---|---|---|
| III | 0.01 | 19.2 | 2.0* | 10.5 |
|  | 0.1 | 20.1 | 1.6* | 8.2 |
|  | 1 | 19.6 | 1.9* | 9.9 |
| IV | 0.01 | 20.4 | 2.4* | 11.5 |
|  | 0.1 | 19.8 | 1.6* | 8.2 |
|  | 1 | 18.7 | 1.2* | 6.0 |
| Control | — | 19.3 | 3.2 | 16.6 |

*(denotes to be significant at 5% level by one-way lay-out analysis of variance.)

TEST EXAMPLE 3

Seeds of rice (variety: Nihonbare) were immersed in a mixed solution of the brassinolide derivative of the formula (III) with 1000-times diluted solution of Benlate T at a concentration of 0.01 ppm of the ingredient at room temperature for 24 hours, and then washed with water and immersed in water for 24 hours. After germination, the seeds were sown on granular soil in a nursery box, covered with the same soil and placed in a budding container for two days. After taken out, they were applied to greening and then cultivated in an air conditioning room at 12° C.–17° C.–22° C., and after growth for 21 days, the plant heights and the dry weights of shoot, root and paddy, respectively, were determined.

As shown by the results in Table 3, increases in plant height and in the dry weights of the shoot over ground and the root part were observed, and so inspite of growth condition at low temperatures of 12° to 22° C., favorable growth was attained by treatment of brassinolide derivative of the formula (III).

TABLE 3

Effect on the early growth of rice seedling by soaking paddy

| Compound | Concentration (ppm) | Plant height (cm) | Dry weight (mg) | | |
|---|---|---|---|---|---|
|  |  |  | Shoot | Root | Paddy |
| [III] | 0.1 | 19.6 | 274.0 | 9.0 | 7.0 |
| Untreated | — | 19.0 | 228.0 | 7.4 | 7.4 |

TEST EXAMPLE 4

Seeds of rice (CV. Nihonbare) were soaked in solutions of the compounds (III),(IV), and tetraacetate of (III) adjusted to the concentrations of 1, 1, and 0.1 ppm respectively, by mixing with a 200 times-diluted solution of Benlate, at room temperature for 24 hours. Then, after washed and dipped with water, at the time of the length of 1 to 2 mm of bud, 30 pieces of the seeds were sown in each concrete pot (50 cm×50 cm) outdoors, and after 30 days the number of budding was observed. (Sewing was conducted on April 20 by 1 cm deep and flooded with water 5 cm deep for cultivation.)

As shown in Table 4, all treated regions were superior to the untreated region in budding.

TABLE 4

Effect on direct sewing of rice

| Compound | Concentration (ppm) | Germination rate (%) |
|---|---|---|
| III | 1.0 | 40.0 |
| IV | 1.0 | 55.0 |
| Tetraacetate of III | 0.1 | 54.5 |
| Untreated | — | 18.3 |

What we claim is:

1. A method for increasing the yield of cereals which comprises applying to said plant an effective amount of at least one selected from the group consisting of a brassinolide derivative of the formulae:

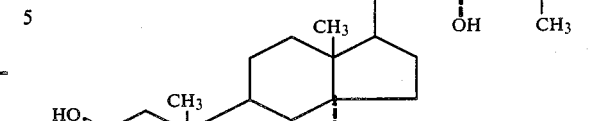

and

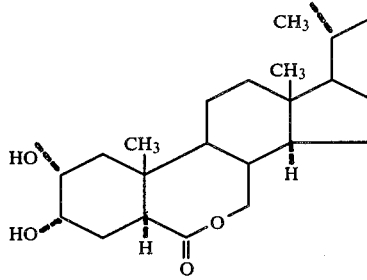

at about the time of flowering.

2. A method according to claim 1, wherein said cereal is wheat.

* * * * *